(12) United States Patent
Arce Guerpero et al.

(10) Patent No.: US 9,066,969 B2
(45) Date of Patent: Jun. 30, 2015

(54) CERAMIC BIOCOMPOSITE FOR BONE REGENERATION

(75) Inventors: Sandra Arce Guerpero, Cali, CO (US); Carlos Humberto Valencia, Cali, CO (US)

(73) Assignee: UNIVERSIDAD AUTONOMA DE OCCIDENTE, Cali (CO)

( * ) Notice: Subject to any disclaimer, the term of this patent is extended or adjusted under 35 U.S.C. 154(b) by 0 days.

(21) Appl. No.: 14/008,176

(22) PCT Filed: Mar. 27, 2012

(86) PCT No.: PCT/IB2012/051467
§ 371 (c)(1),
(2), (4) Date: Dec. 20, 2013

(87) PCT Pub. No.: WO2012/131585
PCT Pub. Date: Oct. 4, 2012

(65) Prior Publication Data
US 2014/0105876 A1 Apr. 17, 2014

(30) Foreign Application Priority Data
Mar. 28, 2011 (CO) .................................. 11-037516

(51) Int. Cl.
| | | |
|---|---|---|
| *A61K 35/32* | (2006.01) | |
| *A61K 31/722* | (2006.01) | |
| *A61L 27/12* | (2006.01) | |
| *A61L 27/36* | (2006.01) | |
| *A61K 45/06* | (2006.01) | |
| *A61L 27/20* | (2006.01) | |
| *A61L 27/24* | (2006.01) | |
| *A61L 27/40* | (2006.01) | |
| *A61L 27/58* | (2006.01) | |
| *C08L 5/08* | (2006.01) | |

(52) U.S. Cl.
CPC .............. *A61K 31/722* (2013.01); *A61L 27/12* (2013.01); *A61L 27/3608* (2013.01); *A61K 45/06* (2013.01); *A61L 27/20* (2013.01); *A61L 27/24* (2013.01); *A61L 27/40* (2013.01); *A61L 27/58* (2013.01); *C08L 5/08* (2013.01)

(58) Field of Classification Search
USPC ........................... 514/55, 17.2; 424/484, 549
See application file for complete search history.

(56) References Cited

U.S. PATENT DOCUMENTS

| | | | |
|---|---|---|---|
| 6,214,048 B1 * | 4/2001 | Ito et al. ..................... 623/16.11 |
| 2004/0127995 A1 * | 7/2004 | Shalaby ..................... 623/23.58 |
| 2007/0123603 A1 | 5/2007 | Shalaby | |
| 2007/0224286 A1 * | 9/2007 | Kutty et al. .................. 424/602 |
| 2009/0270527 A1 * | 10/2009 | Lin et al. ....................... 523/116 |
| 2011/0182995 A1 * | 7/2011 | Asgary ......................... 424/489 |

FOREIGN PATENT DOCUMENTS

| | | | |
|---|---|---|---|
| EP | 0 329 | * | 8/1989 |
| EP | 329098 | | 8/1989 |
| JP | 3261643 | | 11/1991 |

OTHER PUBLICATIONS

Fuentes G. et al. Influence of the Composition on Setting Time and Porosity in Hydroxyapatite Cements with Alginate and Chitosan. Latin American Applied Research 35(4)289-294, 2005.*
Ito, M. et al. In vitro Properties of a Chitosan Bonded Bone Filling Paste. J of Biomedical Materials Research 32(1)95-98, Sep. 1996.*
Kalita S. et al. Nanocrystalline Calcium Phosphate Ceramics in Biomedical Engineering. Materials Science & Engineering C. 27:441-449, 2007.*
Ito, M. et al.; Experimental Development of a Chitosan-bonded Beta-tricalcium Phosphate Bone Filling Paste; Bio-Medical Materials and Engineering, vol. 4, No. 6, pp. 439-449, 1994.

* cited by examiner

*Primary Examiner* — Ralph Gitomer
(74) *Attorney, Agent, or Firm* — Lucas & Mercanti, LLP

(57) ABSTRACT

The invention relates to a ceramic biocomposite for bone regeneration, having a pH range of between 6.5 and 8.5, with an initial plasticity that allows the biocomposite to be easily moulded in situ and to set after 7 minutes, meaning that it can remain at the indicated location during the healing process. In addition, the biocomposite has demonstrated an ability to stimulate bone formation in hard-to-heal wounds. The material can act alone or in combination with other types of bone graft such as autografts, homografts or xenografts which act as a vehicle, as a binding material for endosseous prostheses or as a covering for endosseous implants or prostheses.

4 Claims, 7 Drawing Sheets

CERAMIC BIOCOMPOSITE FOR BONE REGENERATION

CROSS REFERENCE TO RELATED APPLICATION

This Application is a 371 of PCT/IB2012/051467 filed on Mar. 27, 2012, which claims the priority of Colombian Patent Application No. 11-037516 filed on Mar. 28, 2011, both applications are incorporated herein by reference in their entirety.

TECHNICAL FIELD

The present invention refers to a biocomposite to be used in bone regeneration techniques, in which both the stimulation of formation and the increase in the bone volume are sought.

The biocomposite of the present invention has application in the dentistry field, in situations where the bone of the jaw, due to a suffered trauma or by the normal physiological process of bone reabsorption, is not enough for the installation of dental implants or to improve the aesthetics and the function of a dental prosthesis.

The biocomposite of the present invention is also useful in traumatology and orthopedics, when the use of grafts or bone substitutes is needed due to the considerable loss of bone tissue caused by a trauma. In bone surgery, in the treatment of the aftermath of pathological or infectious processed such as the effects caused by benign or malign tumors, as well as osteomyelitis, which generate bone cavities that hardly heal spontaneously.

The biocomposite of the present invention, also known as ceramic biocomposite, features good physical and chemical properties which allow a secure application and facilitate its handling "in-situ", given that it initially allows to me molded and then hardens (setting) in a short but adequate time for the surgery needs, acquiring thereby a consistency rigidly enough to remain in place without being dissolved by the tissue fluids.

The biomaterial is biocompatible, osteoconductive and further, it stimulates the bone formation in places with difficult or impossible spontaneous healing ("critical size" defects), due to its osteopromoting properties. Such properties are evidenced in experimental studies made in animal models to which "critical size" defects were induced, i.e. defects with no spontaneous healing in the entire life of the animal.

BACKGROUND OF THE INVENTION

The bioengineering is in a constant search of substitutes capable of replacing the autologous bone graft.

In developing such materials it is possible to find different bioceramic based products which try to imitate the natural bone, for example document EP0329098 reveals a curable material comprising hydroxyapatite, zinc oxide and/or magnesium oxide, which hardens in a period of 2 to 19 minutes, and maintains a pH in the range of 6 to 8. While this range of pH can be considered as physiological, the hardening interval is too wide, since 2 minutes is just a very short time to achieve a correct placement and a good molding of the material and 19 minutes is too much time for the operation needs in bone surgery.

In addition, the hydroxyapatite, although it is a material with adequate ostoconductive characteristics, features incorporation problems due to the fact that its reabsorption is carried out very slowly.

Document EP0555807 teaches a substitute comprising bovine apatites (Xenograft), mixed with calcium oxide, zinc oxide, magnesium oxide and chitosan. This products exhibits a pH in the range from 6 to 8, which interval can be considered as similar to physiological, the hardening times are prolonged. The product is based on the bovine apatite system, which has excellent osteoconductive properties. However, given the precedence of the apatite, this is not exempt of biohazards and increased the costs of production due to the high costs associated with its processing.

The application U.S. Pat. No. 5,618,339 teaches a bone filler which incorporates an osteoinductive substance. The composed disclosed therein is formed by crystallized hydroxyapatite and amorphous hydroxyapatite, mixed with chitosan. The amorphous substance is obtained from animal bone tissue (bovine), which makes the obtaining process of products from animal species to be wasteful, expensive and not exempt of biohazard.

According to such document, the composite features hardening properties and handles a pH in a physiological range. The base product is hydroxyapatite, which is recognized by its excellent osteoconductivity, but as mentioned above, its origin from the tissue of different species (Xenograft) causes this product to exhibit the same disadvantages as those in the above reference.

According to the same document, the osctoinductive property was tested in experimental defects created in rat calvarial Sprague Dawley, females of 4 weeks old, in a skull defect of 2 mm diameter and a depth of 0.3 mm. It was compared with control defects containing only hydroxyapatite, finding thereby differences in the bone formation. However, as it is sufficiently reported in the specialized literature, in order to test osteoinductive or osteoprmotive properties the defects should be of 5 mm diameter and 0.88 mm depth so as to be qualified as "critical size defects".

In this regard, there is still a non-fulfilled need in the state of the art of a ceramic material featuring the proper physicochemical characteristics which allow an easy molding and setting of the material in order to facilitate the application thereof in bone cavities with difficult healing.

BRIEF DESCRIPTION OF THE INVENTION

The object of the present invention is a synthetic biocomposite based on the tricalcium β-phosphate system, which is a material with a recognized biocompatibility, ostoconductivity, bioactivity and complete reabsorption.

According to the present invention, the tricalcium β-phosphate composite is combined with chitosan which is a natural polymer, exhibiting osteopromoting properties, and with other totally biocompatible products such as zinc oxide and calcium oxide, which allow to adjust the pH in all the formulations to a value ranging from 6.5 to 8.5, which is a range similar to the physiological pH.

The biocomposite of the present invention can be applied combined with other type of grafts as autografts, homografts, xenografts and alloplastic to produce a ceramic biomaterial also being part of the present invention.

The present invention is also directed to the ceramic biomaterial comprising the previously disclosed biocomposite, as vehicle for other substances for bone regeneration such as collagen type osteopromoting substances, bone marrow aspirate and plasma rich in platelets and osteoinductive substances, such as for example, morphogenic proteins among which are transforming growth factor (TGF-β). Moreover, the biocomposite can act as cementitious or coating material in endo-osseous prosthesis.

The biocomposite of the present invention is kept at a reaction temperature of 20° C., with a hardening range from 7 to 15 minutes, obtaining thereby a plasticity which allows a maneuverability "in situ" in times of intra-operative works very convenient for the surgeon.

The properties of biocompatibility and osteoconductivity were tested in a research with an animal model (Oryctolagus cuniculus) in a "critical" size defect in the ilium bone, i.e. in big size surgical preparations which do not spontaneously heal with time.

DETAILED DESCRIPTION OF THE INVENTION

The biocomposite is based on the combination of a solid phase constituted by tricalcium β-phosphate, calcium oxide and zinc oxide which are combined with a liquid phase composed by a natural polymer such as chitosan. This combination provides osteopromoting properties.

The compounds forming the solid phase, according to the present invention, are in the following ranges of weight percentage in relation to the total weight of said solid phase:

| | |
|---|---|
| tricalcium β-phosphate | 92% to 96% |
| Calcium oxide | 2.5% to 6.5% |
| Zinc oxide | 0.5% to 3.5% |

The production procedure of the biocomposite consists in preparing different formulations varying the percentage of the composition in the solid phase and the liquid phase. The amounts of the components in the solid phase are weighed: tricalcium β-phosphate, calcium oxide and zinc oxide, are mixed for 5 minutes and dehydrated in a microwave oven. Then, the necessary amount of chitosan is added and mixing is continued until obtaining a fluid paste.

The solid phase is mostly dry tricalcium β-phosphate with a purity greater than 96%, the other components used in this phase must have a purity greater than 98%.

The liquid phase is composed by natural polymer chitosan gel obtained from crustacean shell at 2%. The chitosan gel is the binding elements of the product of the present invention and it is important in the moldable characteristics of the material. In theory, neutral or acid chitosan can be used. In this invention, chitosan dissolved in acetic acid was used, which is the form as normally used.

Figure 1:
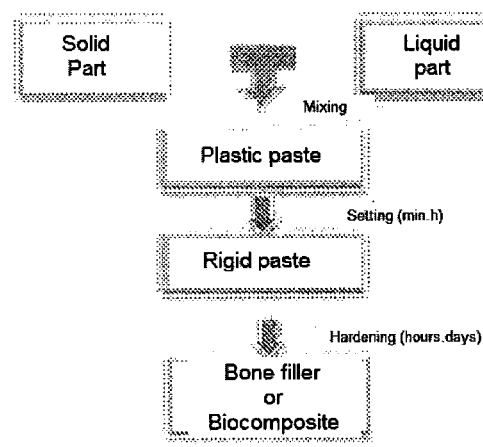
FIG. 1. Shows the flowchart of the methodology used for obtaining the biocomposite.
Figure 2:
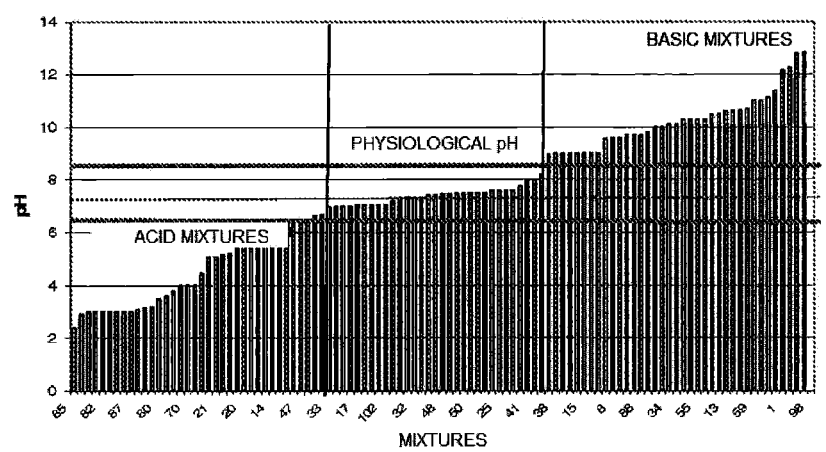
FIG. 2. Shows the pH intervals for different proportions of formulations of tricalcium β-phosphate, calcium oxide, zinc oxide, magnesium oxide and chitosan according to the present invention. The invention is focused on mixtures being in the range of physiological pH.
Figure 3:
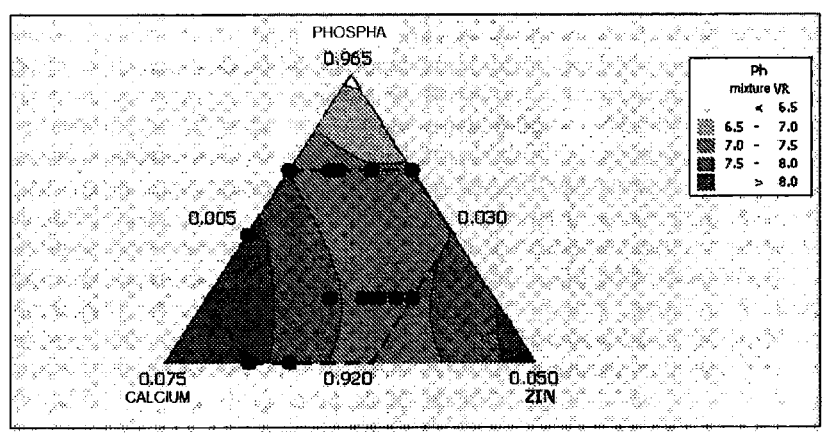
FIG. 3. Shows the surroundings of the three components if the different mixtures for the solid phase.

FIG. 3 shows the surroundings of the mixture and the regions for which the target pH value of 6 is obtained are reported, as well as the lines and black dots of the region described for the experimental samples, according to the present invention.

Such tests were performed at a temperature of 22° C. and a relative humidity of 100%, the pH was measured when the solid phase and the liquid phase were combined and the ph measurements were taken every minute, during 45 minutes from the time in which the homogeneous mixture was obtained.

EXAMPLES

Three mixtures were prepared according to the present invention, which proportions for the solid phase are as follow:

| Mixture B.C1 (example 1) | Mixture B.C3 (example 2) | Mixture B.C4 (example 3) |
|---|---|---|
| Tricalcium phosphate = 96% Calcium oxide = 2.5% Zinc oxide = 1.5% | Tricalcium phosphate = 93% Calcium oxide = 3.5% Zinc oxide = 3.5% | Tricalcium phosphate = 93% Calcium oxide = 4% Zinc oxide = 3% |

In all these, 3 g of chitosan were added as liquid phase.

The preparation process of the biocomposite of the present invention according to the above examples comprises the following steps:

1. Weighing the amounts of zinc oxide, calcium oxide and tricalcium β-phosphate;
2. Placing in a mixer the amounts previously weighed and mixing during a period of 5 to 15 minutes until obtaining a homogeneous combination of the components;
3. Heating in a microwave oven, the mixture obtained in the step 2, during a minute for its dehydration;
4. Weighing the amount of chitosan gel (liquid phase) and adding it to the mixture of minerals obtained in step 3;
5. Mixing from 2 to 5 minutes the products in steps 3 and 4 in the mixer until obtaining the homogeneous preparation.

The calculation for the proportions of the three components in the solid phase, was made through a quadratic model and it is shown in FIG. 3, wherein the surroundings of the mixture and the regions of the pH values required for the application are shown. It was surprisingly found that the compositions where the powder/liquid ratio is 0.67 have adequate physicochemical properties which allow its easy molding and a setting time convenient for the application thereof in bone cavities difficult to heal.

The interval in which the solid phase to liquid phase ratio can range is from 0.5 to 0.9. Preferably, the solid phase to liquid phase ratio corresponds to 0.67, which according to the examples provided in the present specification, is equivalent to 2 g of powder (solid phase) per 3 g of liquid phase.

Such proportion is fundamental because it provides the consistency of application necessary for the material to maintain "in situ" allowing thereby the moldability and the conformation of tissue without the dispersion of the product and without being affected by body fluids. In addition, the powder/liquid proportion is important because it guarantees the mechanical resistance ideal for supporting the load made by the comprehensive and tensional forces generated during the healing process.

Physicochemical Tests for the Biocomposite:

pH Measurement: The pH induced for the formulations of the mixtures was determined with the pH universal meter (a pH meter Accumeter Basic Ab15/15). Such tests were made at a temperature of 22° C. and a relative humidity of 100%. Before each measurement, the pH meter was calibrated with pH patterns dissolutions.

Resistance to Compression

The maximum value to which the material is disintegrated was determined through the use of test tubes which dimensions are 9 mm diameter and 18 mm length, wherein the different mixtures of the biocomposite were placed and after its setting a machine velocity of 1 mm/min was applied. It was recorded that the biocomposite with different proportions according to the present invention has a load tension between 2.100 g/cm$^2$ (2.1×10$^7$ g/m$^2$) and 6.700 g/cm$^2$ (6.7×10$^7$ g/m$^2$).

Biological Tests for the Biocomposite

For the study, 4 month old male New Zealand bunnies were employed and with an average weight of 4.200 grams. 13 animals were distributed in two groups: the first one with 8 animals for histomorphometric studies and the second group with 5 animals for conducting the analysis with electronic microscopy.

An incision was made on the side face of the right prominence and a surgical defect of 6 mm diameter and 3 mm depth was made with a trephine bur and fisiodispenser Novoug for bone implantation. The biocomposite of the present invention was prepared, placed in situ and the tissue by planes was closed with resorbable material. The same procedure was made in the left side but leaving the defect empty. The healing was allowed for 60 days taking into account that the bone remodeling process in bunnies is of 45 days.

After 60 days, the animals were sacrificed and the samples were collected by cutting the hip fragments where the surgical preparations were located. 8 double samples (experimental and control) and 5 double samples were randomly selected for the histomorphometric studies and the electronic microscopy studies, respectively.

The histomorphometric studies showed significant differences in the histodynamics of bone formation between the two groups, the results shows a filling of 100% in mature bone and histological remodeling after sixty days in the group treated with the biocomposite of the present invention, unlike the control group where there was only a partial filling of the defect in a 25% of the cases and with no evidence of bone remodeling.

Meanwhile, the electronic microscopy studies confirm those obtained in the histomorphometric study, given that these evidence the existence of statistically significant differences in the bone formation between the experimental group treated with the biocomposite of the present invention and the control group.

Figure 4:
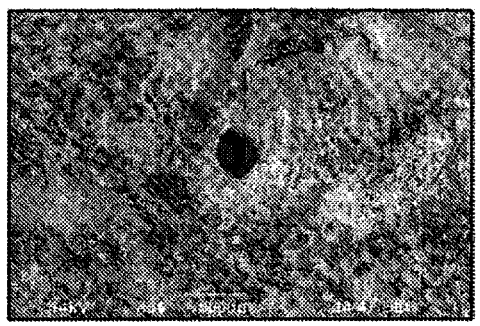
FIG. 4. SEM microphotography illustrating a sample where the bone defect filled with the biocomposite of the invention is almost totally closed by neoformed bone.
Figure 5:
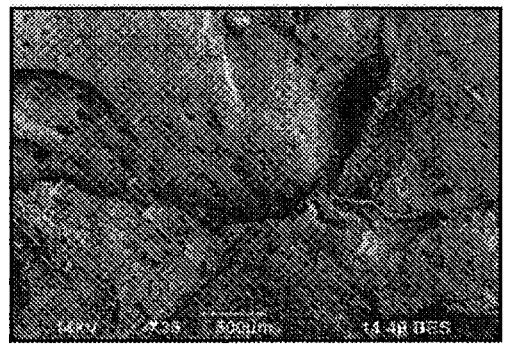
FIG. 5. SEM microphotography illustrating a control sample where the bone defect is invaded by fibrous tissue.
Figure 6:
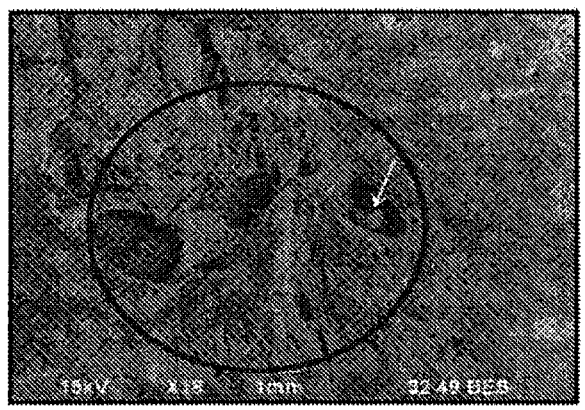
FIG. 6. SEM microphotography showing that the center of the experimental defect treated with the biocomposite of the present invention contains small zones in the regeneration process. In one of such zones a healing nucleolus (arrow) is appreciated.
Figure 7:
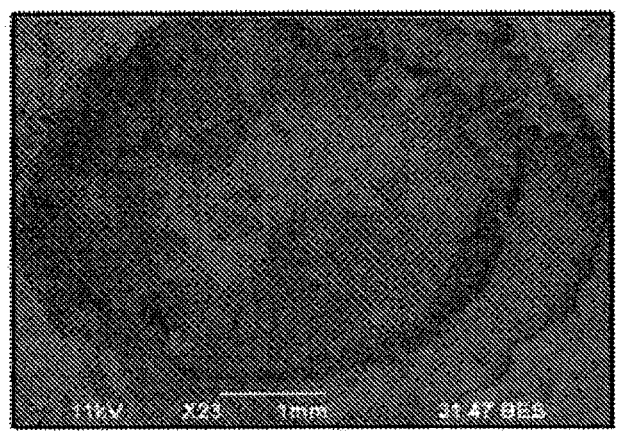
FIG. 7. SEM microphotography wherein the non-bone healing is observed, evidencing only the partial formation of the medium cortical plate.

In FIGS. 4 and 6 it can be seen that the application of the biocomposite of the present invention aids the bone formation in the experimental defect created, which evidences an osteopromoting characteristics of the biocomposite of the present invention, unlike what is shown in FIGS. 5 and 7 corresponding to the control group, wherein it can be seen that the defect is invaded by fibrous tissue with no formation of new bone.

The invention claimed is:

1. A ceramic biocomposite for bone regeneration with a hardening time of from 7 to 15 minutes, which stimulates formation and increase of bone volume, comprising:
    a) a solid phase comprising:
        i. between 93% and 96% of tricalcium β-phosphate in relation to the weight of the total solid phase;
        ii. between 2.5% and 4% of calcium oxide in relation to the total weight of the solid phase; and
        iii. between 1.5% and 3.5% of zinc oxide in relation to the total weight of the solid phase; and
    b) a liquid phase comprising chitosan;
    wherein the solid phase to liquid phase ratio is about 0.67 thereby stimulating formation and increase of bone volume.

2. The ceramic biomaterial comprising a biocomposite according to claim 1 in combination with a graft selected from the group consisting of autografts, homografts, xenografts and alloplastic.

3. The ceramic biomaterial comprising a biocomposite according to claim 1 in combination with osteopromoting substances selected from the group consisting of collagen, bone marrow aspirate and plasma rich in platelets or with osteoinductive substances comprising morphogenetic proteins.

4. The ceramic biomaterial according to claim 3, wherein the morphogenetic proteins are transforming growth factor-beta (TGF-β).

* * * * *